United States Patent [19]

Miesel

[11] 4,293,552

[45] Oct. 6, 1981

[54] NOVEL 1-(MONO-O-SUBSTITUTED BENZOYL)-3-(SUBSTITUTED PYRAZINYL) UREAS

[75] Inventor: John L. Miesel, Indianapolis, Ind.

[73] Assignee: Eli Lilly and Company, Indianapolis, Ind.

[21] Appl. No.: 62,393

[22] Filed: Jul. 31, 1979

Related U.S. Application Data

[63] Continuation-in-part of Ser. No. 881,300, Feb. 27, 1978, abandoned.

[51] Int. Cl.³ ................. C07D 241/20; C07D 241/26; A01N 43/60
[52] U.S. Cl. .................................... 424/250; 544/336; 544/408; 544/409
[58] Field of Search ................ 424/250; 544/336, 408, 544/409

[56] References Cited

U.S. PATENT DOCUMENTS

| | | | |
|---|---|---|---|
| 3,748,356 | 7/1973 | Wellinga | 260/553 E |
| 3,933,908 | 1/1976 | Wellinga | 260/553 E |
| 3,989,842 | 11/1976 | Wellinga | 424/332 |
| 3,992,553 | 11/1976 | Sirrenberg | 260/553 E |
| 4,005,223 | 1/1977 | Sirrenberg et al. | 424/322 |
| 4,160,834 | 7/1979 | Miesel | 424/250 |

FOREIGN PATENT DOCUMENTS 838288 3/1976 Belgium .
838286 8/1976 Belgium .

OTHER PUBLICATIONS

VanDaalen et al., "Die Naturwissen schaften", 59, 312–313 (1972).
Post et al., "Die Naturwissenschaften", 60, 431–432 (1973).
Mulden et al., "Pestic. Sci."-vol. 4 737–745, (1973).
Jakob, "J. Med. Ent.", 10, 452–455 (1973).
Noal, Jr., "J. Econ. Ent.", 67, 300–301 (1974).

*Primary Examiner*—Mark L. Berch
*Attorney, Agent, or Firm*—Dwight E. Morrison; Arthur R. Whale

[57] ABSTRACT

Novel 1-(mono-o-substituted benzoyl)-3-(substituted pyrazinyl) ureas, active as insecticides, and methods for their use as insecticides.

22 Claims, No Drawings

NOVEL 1-(MONO-O-SUBSTITUTED BENZOYL)-3-(SUBSTITUTED PYRAZINYL) UREAS

CROSS-REFERENCE

This is a continuation-in-part of my copending application Ser. No. 881,300, filed Feb. 27, 1978, now abandoned.

BACKGROUND OF THE INVENTION

1. Field of the Invention

The control of insects is of vital importance in the increasingly populous world of today. It is well known that insects such as those belonging to the orders of Lepidoptera, Coleoptera, Diptera, Homoptera, Hemiptera and Orthoptera, at the larval stage, cause extensive damage to many crops, for example, food crops and fibrous crops. Control of such insects contributes to the well-being of mankind by increasing the supplies of food and of the fibrous materials useful in the production of clothing.

2. Description of the Prior Art

In the prior art, Wellinga et al., U.S. Pat. No. 3,748,356 (July 24, 1973), describe a series of substituted benzoylureas which are taught as having strong insecticidal activity. The Wellinga et al. compounds are generally 1-(2,6-dichlorobenzoyl)-3-substituted phenyl)ureas, but also include several 1-(2,6-dichlorobenzoyl)-3-(substituted pyridyl)ureas.

Also in the prior art, Wellinga et al., U.S. Pat. No. 3,989,842 (Nov. 2, 1976), teach and claim insecticidal compositions and a method of controlling insects in agriculture and horticulture utilizing certain N-(2,6-dihalobenzoyl)-N'-(substituted phenyl)urea compounds as the active ingredient, as well as several N-(2,6-dichlorobenzoyl)-N'-(substituted pyridyl)ureas.

Other N-(2,6-dihalobenzoyl)-N'-(substituted phenyl)urea compounds are disclosed and claimed in Wellinga et al., U.S. Pat. No. 3,933,908 (Jan. 20, 1976), which compounds are disclosed as having insecticidal activity.

A number of prior art references discuss the insecticidal activity of 1-(2,6-dichlorobenzoyl)-3-(3,4-dichlorophenyl)urea. See Van Daalen et al., *Die Naturwissenschaften* 59, 312–313 (1972); Post et al., ibid. 60, 431–432 (1973); Mulder et al., *Pestic. Sci.* 4, 737–745 (1973).

Also, studies in the inhibition of the development of mosquitoes and houseflies, and of the control of alfalfa weevil, by the action of 1-(4-chlorophenyl)-3-(2,6-difluorobenzoyl)urea are reported by Jakob, *J. Med. Ent.* 10. 452–455 (1973), and Neal, Jr., *J. Econ. Ent.*, 67, 300–301 (1974), respectively.

Yet another prior art reference is Sirrenberg et al., U.S. Pat. No. 3,992,553 (Nov. 16, 1976), which discloses and claims mono-o-chloro-substituted benzoylureidodiphenyl ethers, alleged to posses excellent insecticidal activity against plant pests and as ectoparasitic agents in the veterinary medicine field.

Also in the prior art is Belgian Pat. No. 833,288 (Mar. 11, 1976), which teaches and claims disubstituted benzoyl pyrazinylureas having activity as insecticides.

Still another prior art reference is Belgian Pat. No. 838,286, directed to 1-benzoyl-3-(4-phenoxyphenyl-)ureas alleged to possess insecticidal activity with low mammalian and plant toxicity.

SUMMARY OF THE INVENTION

This invention is directed to novel 1-(mono-o-substituted benzoyl)-3-(substituted pyrazinyl)ureas having insecticidal activity, and to methods of use of the novel compounds.

DESCRIPTION OF THE PREFERRED EMBODIMENT

The present invention relates to novel 1-(mono-o-substituted benzoyl)-3-(substituted pyrazinyl)ureas of the formula

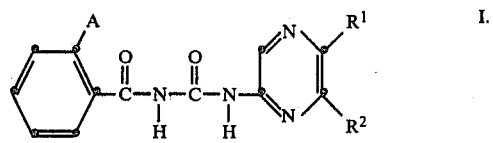

wherein
A is bromo, chloro, or methyl;
$R^1$ is hydrogen, halo, $C_3$–$C_6$ cycloalkyl, halo($C_1$–$C_4$)alkyl, nitro, cyano,

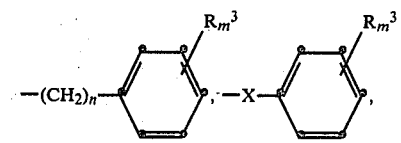

or naphthyl;
$R^2$ is hydrogen, halo, methyl, ethyl, cyano, or halo($C_1$–$C_2$)alkyl;
with the limitation that $R^1$ and $R^2$ may not both be hydrogen at the same time;
$R^3$ is hydrogen, halo, halo($C_1$–$C_4$)alkyl, $C_1$–$C_6$ alkyl, $C_1$–$C_4$ alkoxy, $C_1$–$C_4$ alkylthio, $C_1$–$C_4$ alkylsulfinyl, $C_1$–$C_4$ alkylsulfonyl, nitro, cyano, phenoxy, or phenyl;
m is 0, 1, 2, or 3;
n is 0 or 1; and
X is —O—, —S—,

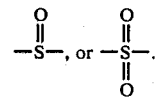

Preferred compounds coming within the scope of the above generic formula I are those wherein
A is bromo, chloro, or methyl;
$R^1$ is hydrogen, halo, $C_3$–$C_6$ cycloalkyl, halo($C_1$–$C_4$)alkyl,

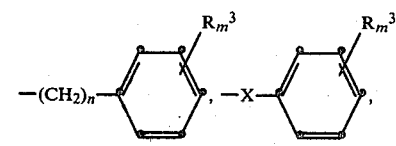

or naphthyl;
$R^2$ is hydrogen, halo, methyl, ethyl, or halo($C_1$–$C_2$)alkyl;
with the limitation that $R^1$ and $R^2$ may not both be hydrogen at the same time;

$R^3$ is halo, halo($C_1$–$C_4$)alkyl, $C_1$–$C_6$ alkyl, $C_1$–$C_4$ alkoxy, $C_1$–$C_4$ alkylthio, $C_1$–$C_4$ alkylsulfinyl, $C_1$–$C_4$ alkylsulfonyl, nitro, or cyano;
m is 0, 1, 2, or 3;
n is 0 or 1; and
X is —O—, —S—,

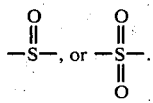

The more preferred compounds coming within the scope of the above generic formula I are those wherein
A is bromo, chloro, or methyl;
$R^1$ is halo, halo($C_1$–$C_2$)alkyl, $C_3$–$C_6$ cycloalkyl,

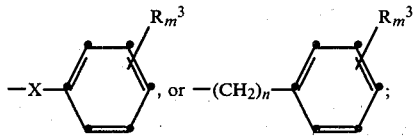

$R^2$ is hydrogen, halo, halo($C_1$–$C_2$)alkyl, or methyl;
$R^3$ is hydrogen, halo, halo($C_1$–$C_2$)alkyl, $C_1$–$C_2$ alkyl, or $C_1$–$C_2$ alkoxy;
m is 0, 1, or 2;
n is 0 or 1; and
X is —O— or —S—.

The most preferred compounds coming within the scope of the above generic formula I are those wherein
A is bromo, chloro, or methyl;
$R^1$ is

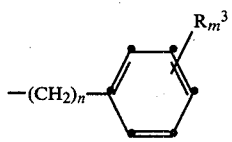

or cyclohexyl;
$R^3$ is halo, halo($C_1$–$C_2$)alkyl, $C_1$–$C_2$ alkyl, or $C_1$–$C_2$ alkoxy;
n is 0;
m is 1 or 2;
$R^2$ is hydrogen or methyl; with the proviso that when $R^2$ is H, and m is 1, $R^3$ must be chloro or bromo in the para position.

In the generic formula above, halo refers to fluoro, chloro, and bromo.

$C_3$–$C_6$ Cycloalkyl represents saturated cycloalkyl having from 3 to 6 carbon atoms in the ring and is exemplified by cyclopropyl, cyclobutyl, cyclopentyl and cyclohexyl.

Halo($C_1$–$C_4$)alkyl represents trifluoromethyl, bromomethyl, 1,1-difluoroethyl, pentafluoroethyl, 1,1,2,2-tetrafluoroethyl, chlorodifluoromethyl, trichloromethyl, 2-bromoethyl, chloromethyl, 3-bromopropyl, 4-bromobutyl, 3-chloropropyl, 3-chlorobutyl, and the like.

Halo($C_1$–$C_2$)alkyl refers to trifluoromethyl, bromomethyl, chloromethyl, 1,1-difluoroethyl, pentafluoroethyl, 1,1,2,2-tetrafluoroethyl, chlorodifluoromethyl, trichloromethyl, 2-bromoethyl, and the like.

$C_1$–$C_2$ Alkoxy represents methoxy or ethoxy.

$C_1$–$C_4$ Alkoxy represents methoxy, ethoxy, propoxy, isopropoxy, n-butoxy, sec.-butoxy, isobutoxy, or t-butoxy.

$C_1$–$C_2$ Alkylthio represents methylthio or ethylthio.

$C_1$–$C_4$ Alkylthio represents methylthio, ethylthio, n-propylthio, isopropylthio, n-butylthio, isobutylthio, sec.-butylthio, or t-butylthio.

$C_1$–$C_4$ Alkylsulfonyl represents methylsulfonyl, ethylsulfonyl, n-propylsulfonyl, isopropylsulfonyl, butylsulfonyl, and the like.

$C_1$–$C_4$ Alkylsulfinyl represents methylsulfinyl, ethylsulfinyl, n-propylsulfinyl, isopropylsulfinyl, butylsulfinyl, and the like.

Novel compounds coming within the scope of the generic formula I above include, but are not limited to the following:

1-(2-Bromobenzoyl)-3-[5-($\alpha,\alpha,\alpha$-trifluoro-m-tolyl)-6-methyl-2-pyrazinyl]urea
1-(2-Methylbenzoyl)-3-[5-($\alpha,\alpha,\alpha$-trifluoro-p-tolyl)-6-methyl-2-pyrazinyl]urea
1-[5-($\alpha,\alpha,\alpha$-trifluoro-m-tolyl)-2-pyrazinyl]-3-(2-chlorobenzoyl)urea
1-(5-Chloro-6-methyl-2-pyrazinyl)-3-(2-chlorobenzoyl)urea
1-(5-Bromo-6-ethyl-2-pyrazinyl)-3-(2-methylbenzoyl)urea
1-(2-Bromobenzoyl)-3-[5-($\alpha,\alpha,\alpha$-trifluoro-p-tolyl)-2-pyrazinyl]urea
1-(6-Bromo-5-cyano-2-pyrazinyl)-3-(2-chlorobenzoyl)urea
1-(5-Cyclopentyl-6-methyl-2-pyrazinyl)-3-(2-methylbenzoyl)urea
1-[5-(2-Bromoethyl)-2-pyrazinyl]-3-(2-bromobenzoyl)urea
1-(5-Benzyl-6-chloro-2-pyrazinyl)-3-(2-methylbenzoyl)urea
1-(2-Chlorobenzoyl)-3-(5-phenylthio-2-pyrazinyl)urea
1-(2-Bromobenzoyl)-3-(6-methyl-5-benzyl-2-pyrazinyl)urea
1-(2-Chlorobenzoyl)-3-[5-(1-naphthyl)-2-pyrazinyl]urea
1-(2-Chlorobenzoyl)-3-(6-cyano-5-phenyl-2-pyrazinyl)urea
1-(2-Chlorobenzoyl)-3-(5-nitro-2-pyrazinyl)urea
1-(2-Chlorobenzoyl)-3-[5-(4-chlorophenylthio)-6-methyl-2-yrazinyl]urea
1-(2-Methylbenzoyl)-3-[5-(4-bromophenoxy)-2-pyrazinyl)]urea.

The novel compounds of formula I have been found to be active as insecticides by their action in interfering with the growth of sensitive insects. The compounds appear to interfere with the molting process of the insects and thus cause death. The compounds have been found to act on the insects as a result of the insects ingesting the compounds, e.g., by ingesting the leaves and foliage treated with the active compounds, or ingesting any other part of their normal habitat, e.g., water, manure, and the like, to which the active compounds have been applied. Because of this property, the compounds are useful in a novel method of controlling insects at the larval stage.

The novel compounds of formula I unexpectedly and surprisingly show systemic activity in plants to which the compounds are applied. Thus, when one of the novel insecticidal compounds is applied to an old leaf on a plant, such as a soybean plant, it is found the insecticidal compound is translocated in the soybean plant to the new growth of the plant, and even down the main stem of the plant. However, there is no systemic translocation of the insecticidal compound if the compound is applied to the roots of the soybean or other plant.

Further it has been found that compounds coming within the scope of generic formula I, supra, and having ovicidal activity are those wherein A is bromo or chloro;

R$^1$ is hydrogen, trifluoromethyl, or

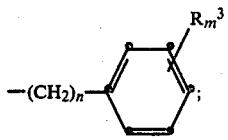

R$^2$ is hydrogen, chloro, methyl, or trifluoromethyl;
R$^3$ is hydrogen, halo, methoxy, trifluoromethyl, or phenyl;
m is 0 or 1; and
n is 0.

The novel compounds of formula I are prepared by procedures known to the art.

Thus, in general, the novel compounds are prepared by allowing a 2-substituted-benzoylisocyanate to react with an aminopyrazine, or by allowing a 2-substituted benzamide to react with a pyrazinylisocyanate, to yield the desired 1-(2-substituted benzoyl)-3-(substituted 2-pyrazinyl)urea.

Some of the starting materials are commercially available, others are prepared by utilizing procedures which are known to the art.

The 2-substituted-benzoylisocyanates are readily prepared from, for instance, 2-substituted benzamides, following the general procedure of Speziale et al., *J. Org. Chem.* 27, 3742 (1962).

One of the intermediates, 2-amino-5-chloropyrazine is prepared following the general procedure of Palamidessi and Bernardi, *J. Org. Chem.* 29, 2491 (1964), wherein methyl 2-amino-3-pyrazinylcarboxylate is allowed to react with chlorine in acetic acid to yield methyl 2-amino-5-chloro-3-pyrazinylcarboxylate. This ester is hydrolyzed with aqueous sodium hydroxide to yield 2-amino-3-carboxy-5-chloropyrazine, which is then heated in tetrahydronaphthalene and decarboxylated to yield the desired 2-amino-5-chloropyrazine.

Another intermediate, 2-amino-5,6-dichloropyrazine, is prepared by allowing 2-amino-6-chloropyrazine to react with N-chlorosuccinimide in chloroform to yield a mixture of 2-amino-5,6-dichloropyrazine, 2-amino-3,6-dichloropyrazine, and 2-amino-3,5,6-trichloropyrazine. The mixture is then separated by column chromatography and the desired 2-amino-5,6-dichloropyrazine is obtained.

The 2-amino-5-phenylpyrazine necessary for this work is prepared according to the procedure of Lont et al., *Rec. Trav. Chim.* 92, 455 (1973), and references therein.

Other 2-amino-5(or 6)-substituted pyrazines useful in preparing the novel final compounds of formula I are prepared utilizing oxime derivatives of certain ketones. Oxime intermediates are prepared from such ketones as acetophenone, 4-trifluoromethylacetophenone, 4-fluoroacetophenone, 2,4-dimethylacetophenone, 4-n-butylacetophenone, 4-chloroacetophenone, and m-trifluoromethylacetophenone, following the general procedure of Claisen et al., *Chem. Ber.* 20, 2194 (1887). Still other oxime intermediates are prepared from ketones such as 4-methoxypropiophenone, 4-trifluoromethylpropiophenone, 4-fluoropropiophenone, 4-n-butylpropiophenone, 4-bromobutyrophenone, and 4-bromopropiophenone, following the general procedure of Hartung et al., *J. Am. Chem. Soc.* 51, 2262 (1929).

Another intermediate pyrazine compound, 2-amino-5-(4-bromophenyl)-6-methylpyrazine, is synthesized starting with 1-(4-bromophenyl)-1,2-propanedione 2-oxime, which oxime is obtained by the same general procedure of Hartung et al., supra. This oxime is allowed to react with aminomalononitrile tosylate, and the product, the substituted pyrazine 1-oxide, is allowed to react with phosphorus trichloride in tetrahydrofuran, according to the procedure of Taylor et al., *J. Org. Chem.* 38, 2817 (1973), to yield 2-amino-3-cyano-5-(4-bromophenyl)-6-methylpyrazine. This product is then hydrolyzed in sodium hydroxide and ethylene glycol and the 2-amino-3-carboxy-5-(4-bromophenyl)-6-methylpyrazine so obtained is decarboxylated by heating in tetrahydronaphthalene to yield 2-amino-5-(4-bromophenyl)-6-methylpyrazine.

Still other pyrazine intermediate compounds can be prepared starting with 2,5-dichloropyrazine, which itself can be prepared by the procedure of Palamidessi and Bernardi, *J. Org. Chem.* 29, 2491 (1964). This 2,5-dichloropyrazine can be used as the starting material for the phenoxy-, phenylthio-, phenylsulfinyl-, or phenylsulfonyl-substituted pyrazine intermediates, or the corresponding substituted-phenoxy-, substituted-phenylthio-, or substituted-phenylsulfonyl-substituted pyrazine intermediates. Thus, as a general procedure, 2,5-dichloropyrazine can be allowed to react with an equivalent of phenoxide or thiophenoxide ion in a suitable solvent such as ethanol, t-butanol, dimethylformamide, acetonitrile, or the like, at a temperature in the range of from about 0° to about 120° C., to yield the corresponding 2-chloro-5-phenoxy(or phenylthio)pyrazine. The 2-chloro-5-phenoxy(or phenylthio)pyrazine can be converted to the corresponding 2-amino-5-phenoxy(or phenylthio)pyrazine by reaction with ammonium hydroxide at a temperature in the range of about 150°-200° C. in a high pressure reaction vessel for a time sufficient to give substantially complete conversion. The 2-amino-5-phenoxy(or phenylthio)pyrazine obtained in this manner can then be used to prepare the 1-(mono-o-substituted benzoyl)-3-[5-phenoxy(or phenylthio)2-pyrazinyl]ureas. Substituted phenoxy- or phenylthio compounds can be prepared in the same general manner.

The 2-chloro-5-phenylthiopyrazine intermediate, or homologue thereof, can be oxidized to the 2-chloro-5-phenylsulfinylpyrazine or the 2-chloro-5-phenylsulfonylpyrazine intermediate through the use of such oxidizing agents as peracetic acid or m-chloroperbenzoic acid. Suitable solvents for use in carrying out this reaction include acetic acid, chloroform, or methylene chloride. Suitable reaction temperatures for the oxidation can range from about 20° to about 70° C.

The 2-chloro-5-phenylsulfonylpyrazine or 2-chloro-5-phenylsulfinylpyrazine can then be allowed to react with ammonia or ammonium hydroxide in a high pressure reaction vessel, at a temperature of about 100° to about 200° C. to yield the 2-amino-5-phenylsulfonyl- or-sulfinylpyrazine intermediate. Reaction conditions may vary depending on the chemical structure of the phenylsulfonyl or phenylsulfinyl grouping.

The novel compounds of formula I are prepared by allowing the 2-aminopyrazine intermediate compounds to react with a 2-substituted-benzoyl isocyanate to yield the corresponding 1-(mono-o-substituted benzoyl)-3-(substituted pyrazinyl)urea. The reaction is carried out at a temperature of from about 0° to about 70° C., suitably at about room temperature, for a sufficient period of time to bring about substantial completion of the reaction. Such time of reaction appears to depend on the particular reactants and can range from the time during which one of the reactants is added to and mixed with the other to 48 hours. The reaction is carried out using a suitable solvent. A suitable solvent is one which is inert to and will not react with the isocyanate compounds used in any of these reactions. Exemplary solvents include, but are not limited to ethyl acetate, dimethylformamide, tetrahydrofuran, dioxane, acetonitrile, benzene, toluene, chloroform, or methylene chloride. The preparation is exemplified as follows: 2-chlorobenzoylisocyanate is allowed to react with 2-amino-5-(4-bromophenyl)-6-methylpyrazine in cold ethyl acetate. The reaction mixture is stirred overnight at room temperature. The product is isolated by filtering, and is purified by recrystallization from a suitable solvent such as ethanol. There is obtained a product having a melting point of about 230°-232° C., which product is identified by elemental analyses and NMR and infrared spectra as 1-(2-chlorobenzoyl)-3-[5-(4-bromophenyl-6-methyl-2-pyrazinyl]urea.

A compound of formula I may also be prepared by allowing a 2-substituted benzamide to react with a 2-pyrazinylisocyanate utilizing the appropriate solvents, times of reaction and general reaction conditions hereinabove described. For example, 2-chlorobenzamide is allowed to react with 5-trifluoromethylpyrazin-2-ylisocyanate to yield 1-(2-chlorobenzoyl)-3-(5-trifluoromethyl-2-pyrazinyl)urea, having a melting point of about 219°-220° C.

The preparations of the intermediate substituted benzoylisocyanates and pyrazines are illustrated by the following Preparations.

Preparation 1

2-Chlorobenzoylisocyanate

This compound was prepared following the procedure of Speziale et al, *J. Org. Chem.* 27, 3742 (1962).

A solution of 10 g. of 2-chlorobenzamide (commercially available) in 100 ml. of methylene dichloride was prepared. Twenty-five ml. of oxalyl chloride was added very slowly to the solution. The mixture was refluxed overnight. The reaction product mixture was cooled and filtered and the filtrate evaporated to remove the solvent, methylene dichloride. The oily residue was identified by infrared spectrum as 2-chlorobenzoylisocyanate, and was used without purification in preparing the novel compounds of formula I.

Following the same general procedure of Preparation 1, and starting with 2-methylbenzamide or 2-bromobenzamide, both of which compounds are commercially available, the following additional compounds were prepared and identified by their IR spectra:

2. 2-Methylbenzoylisocyanate, as an oil.
3. 2-Bromobenzoylisocyanate, as an oil.

Preparation 4

2-Amino-5-chloropyrazine

This compound was prepared stepwise. The first step followed the procedure of Dallacker et al., *Ann.* 660, 98–103 (1962).

Following that procedure, a mixture of 7.5 g. of 2-amino-3-carboxypyrazine, 8.9 g. of 1-methyl-3-p-tolyltriazene, and 250 ml. of tetrahydrofuran was refluxed for about 4 hours. The reaction product mixture was cooled and filtered and the solid on the filter discarded. The filtrate was concentrated in vacuo to dryness and a small amount of ethyl ether was added to the residue. The solid which separated was collected. It weighed about 7 g. and had a melting point of about 166°-169° C. It was identified by infrared spectrum as methyl 2-amino-3-pyrazinylcarboxylate.

In the next step, a mixture of 2.8 g. of methyl 2-amino-3-pyrazinylcarboxylate, 100 ml. of water, and 23 ml. of glacial acetic acid was stirred at a temperature of about 40° C., and anhydrous chlorine bubbled through the mixture for about 25 minutes, while maintaining the temperature of the reaction mixture at about 35°-40° C. The reaction product mixture was cooled and filtered. The solid obtained was stirred for an hour in a mixture of 30 ml. of water and 4.6 g. of sodium sulfite, and filtered off. The solid which was collected was stirred in a mixture of ice and water and filtered off. The solid was identified by its NMR spectrum as methyl 2-amino-5-chloro-3-pyrazinylcarboxylate. The material was used without further purification.

Following the procedure of Palamidessi and Bernardi, *J. Org. Chem.* 29, 2491 (1964), the methyl 2-amino-5-chloro-3-pyrazinylcarboxylate was first hydrolyzed and then decarboxylated.

A mixture of 1.6 g. of methyl 2-amino-5-chloro-3-pyrazinylcarboxylate and 50 ml. of 2 N aqueous sodium hydroxide was refluxed for about 1.5 hours. The reaction product mixture was cooled and filtered. The solid which was collected was dissolved in 25 ml. of hot water, the solution filtered, and the filtrate acidified with concentrated aqueous hydrochloric acid. The solid which separated was filtered off and dried. It weighed 1.3 g., had a melting point of about 177° C. (dec.), and was identified by its infrared spectrum as 2-amino-3-carboxy-5-chloropyrazine. It was used without further purification.

A mixture of 500 mg. of 2-amino-3-carboxy-5-chloropyrazine and 9 ml. of tetrahydronaphthalene was refluxed for about 1 hour. The reaction product mixture was cooled and filtered. The solid which was collected was washed with hexane. The solid had a melting point of about 121°-123° C. (dec.), and was identified by NMR spectrum as 2-amino-5-chloropyrazine.

Preparation 5

2-Amino-5,6-dichloropyrazine

A mixture of 5 g. of 2-amino-6-chloropyrazine (commercially available), 10.3 g. of N-chlorosuccinimide, and 100 ml. of chloroform was refluxed for about 1.5 hours. The reaction mixture was cooled and filtered, the solid collected on the funnel being discarded. The filtrate was evaporated and the residue washed with water and hot aqueous sodium bisulfite solution, and the solid which formed under this treatment was collected on a funnel. The solid was chromatographed on a column of 5×8 mm. styrene and divinylbenzene copolymer beads using chloroform as solvent and eluant. There were obtained by this chromatography three compounds:

Compound 1, having a melting point of about 132°–135° C., was identified as 2-amino-3,6-dichloropyrazine.

Compound 2, having a melting point of about 132°–134° C., was identified as 2-amino-3,5,6-trichloropyrazine.

Compound 3, having a melting point of about 143°–144° C., was identified as 2-amino-5,6-dichloropyrazine, the desired compound.

Preparation 6

2-Amino-5-phenyl-6-methylpyrazine

This intermediate pyrazine was prepared via a stepwise procedure.

In the first step, a mixture of 6.5 g. of 1-phenyl-1,2-propanedione-2-oxime (commercially available) and 10.1 g. of aminomalononitrile tosylate in 60 ml. of isopropyl alcohol was stirred overnight at room temperature. The reaction product mixture was filtered. The solid which was collected weighed 7 g. The solid was identified by NMR spectrum as 2-amino-3-cyano-5-phenyl-6-methylpyrazine 1-oxide.

A mixture of 7 g. of the pyrazine 1-oxide (prepared above) and 250 ml. of tetrahydrofuran was cooled to about 0° C., and 40 ml. of phosphorus trichloride was added slowly thereto. After addition was complete, the reaction mixture was stirred overnight at room temperature. The mixture was then concentrated in vacuo to a volume of about 50 ml., and the concentrate poured into one liter of a mixture of ice and water. The solid which precipitated was collected on a filter. The solid weighed 1 gram and was identified as 2-amino-3-cyano-5-phenyl-6-methylpyrazine.

In the next step, a mixture of 1 g. of the 2-amino-3-cyano-5-phenyl-6-methylpyrazine (prepared above), 50 ml. of ethylene glycol, and 500 mg. of sodium hydroxide was heated at about 150° C. for about 3 hours. The reaction product mixture was cooled, water was added, and the mixture neutralized to a pH of 5–7. The solid which precipitated was collected, and was identified by IR spectrum as 2-amino-3-carboxy-5-phenyl-6-methylpyrazine. This solid was used in the next step of the preparation.

The carboxypyrazine (prepared above), 500 mg., was refluxed in 5 ml. of tetrahydronapthalene for about 2 hours. The reaction product mixture was cooled and hexane added thereto. The solid which precipitated was filtered off. It weighed 470 mg., and was identified by NMR and IR spectra as 2-amino-5-phenyl-6-methylpyrazine.

Following the same general procedure described in Preparation 6, and using as starting materials the indicated oximes, prepared as described by Hartung et al., *J. Am. Chem. Soc.* 51, 2262 (1929), additional pyrazine intermediates were prepared. These pyrazine intermediates were identified by NMR and IR spectra:

7. 2-Amino-5-(4-methoxyphenyl)-6-methylpyrazine, from 1-(4-methoxyphenyl)-1,2-propanedione-2-oxime.
8. 2-Amino-5-(4-chlorophenyl)-6-methylpyrazine, from 1-(4-chlorophenyl)-1,2-propanedione-2-oxime.
9. 2-Amino-5-(4-bromophenyl)-6-methylpyrazine, from 1-(4-bromophenyl)-1,2-propanedione-2-oxime.
10. 2-Amino-5-(4-n-butylphenyl)-6-methylpyrazine, from 1-(4-n-butylphenyl)-1,2-propanedione-2-oxime.
11. 2-Amino-5-($\alpha,\alpha,\alpha$-trifluoro-m-tolyl)-6-methylpyrazine, from 1-($\alpha,\alpha,\alpha$-trifluoro-m-tolyl)-1,2-propanedione-2-oxime.
12. 2-Amino-5-(4-biphenylyl)-6-methylpyrazine, from 1-(4-biphenylyl)-1,2-propanedione-2-oxime.
13. 2-Amino-5-(4-fluorophenyl)-6-methylpyrazine, from 1-(4-fluorophenyl)-1,2-propanedione-2-oxime.
14. 2-Amino-5-($\alpha,\alpha,\alpha$-trifluoro-p-tolyl)-6-methylpyrazine, from 1-($\alpha,\alpha,\alpha$-trifluoro-p-tolyl)-1,2-propanedione-2-oxime.
15. 2-Amino-5-(4-ethylphenyl)-6-methylpyrazine, from 1-(4-ethylphenyl)-1,2-propanedione-2-oxime.
16. 2-Amino-5-cyclohexyl-6-methylpyrazine from 1-cyclohexyl-1,2-propanedione-2-oxime.
17. 2-Amino-5-(4-methylthiophenyl)-6-methylpyrazine, from 1-(4-methylthiophenyl)-1,2-propanedione-2-oxime.
18. 2-Amino-6-methyl-5-(p-tolyl)pyrazine, from 1-(p-tolyl)-1,2-propanedione-2-oxime.

Following the same general procedure described in Preparation 6, and using oximes prepared by the method of Claisen et al., *Chem. Ber.* 20, 2194 (1887), the following additional pyrazine intermediates were prepared, and identified by NMR and IR spectra:

19. 2-Amino-5-(2,4-xylyl)pyrazine, from 2,4-xylylglyoxal oxime.
20. 2-Amino-5-(3,4-dichlorophenyl)pyrazine, from 3,4-dichlorophenylglyoxal oxime.
21. 2-Amino-5-($\alpha,\alpha,\alpha$-trifluoro-m-tolyl)pyrazine, from 3-trifluoromethylphenylglyoxal oxime.
22. 2-Amino-5-(p-tolyl)pyrazine, from p-tolylglyoxal oxime.
23. 2-Amino-5-(4-chlorophenyl)pyrazine, from 4-chlorophenylglyoxal oxime.
24. 2-Amino-5-(4-ethylphenyl)pyrazine, from 4-ethylphenylglyoxal oxime.
25. 2-Amino-5-(4-t-butylphenyl)pyrazine, from 4-t-butylphenylglyoxal oxime.
26. 2-Amino-5-(4-bromophenyl)pyrazine, from 4-bromophenylglyoxal oxime.

Preparation 27

2-Amino-5-(4-bromophenyl)-6-ethylpyrazine

This intermediate pyrazine was prepared stepwise.

Using 4-bromobutyrophenone as starting material, and following the procedure of Hartung et al., supra, there was prepared 1-(4-bromophenyl)-1,2-butanedione 2-oxime, identified by IR and NMR spectrum.

Following the general procedure of Preparation 6, the 1-(4-bromophenyl)-1,2-butanedione 2-oxime was used to prepare 2-amino-5-(4-bromophenyl)-6-ethylpyrazine, identified by IR and NMR spectrum.

Preparation 28

2-Amino-6-cyanopyrazine

This intermediate was prepared via a stepwise procedure.

A mixture of 21 g. of pyrazine-2-carboxamide, 85 ml. of glacial acetic acid, and 75 ml. of 30 percent hydrogen peroxide was heated at about 55° C. for about 35 hours.

The reaction product mixture was cooled and filtered. The solid which was collected was extracted with n-butanol and the extracts discarded. The solid which was insoluble in n-butanol was recrystallized from hot water to yield a white solid having a melting point of about 302°–305° C. The solid was identified by elemental analyses as pyrazine-2-carboxamide 4-oxide.

To a mixture of 4 g. of the pyrazine oxide (prepared above) in 40 ml. of dimethylformamide cooled in an ice bath, there was quickly added 12 ml. of phosphorus oxychloride. The reaction mixture was poured into water and the aqueous mixture extracted with ethyl acetate, and the extracts saved. Additional water was added to the aqueous layer and the aqueous mixture extracted with hexane-ether. The ethyl acetate and hexane-ether extracts were combined and concentrated in vacuo to leave a residue. The residue was identified by elemental analyses and IR spectrum as 2-chloro-6-cyanopyrazine, and was used without further purification in the next step.

A mixture of 1 g. of the above chlorocyanopyrazine and 25 ml. of dimethyl sulfoxide was prepared and anhydrous ammonia was bubbled thereinto. The reaction mixture was stirred overnight and then poured into water. The aqueous mixture was extracted with ethyl acetate, and the extracts dried. The drying agent was filtered off and the solvent removed in vacuo to leave a solid which was identified by its IR spectrum as 2-amino-6-cyanopyrazine. It was used as is without further purification in the preparation of final products of the invention.

Preparation 29

2-Amino-6-trifluoromethylpyrazine

This intermediate compound was prepared stepwise.

Aminoacetamide dihydrobromide was prepared and identified according to the procedure of Mengelberg, *Chem. Ber.* 89, 1185 (1956). The preparation of 3,3-dibromo-1,1,1-trifluoropropanone was accomplished according to the procedure of McBee and Burton, *J. Am. Chem. Soc.* 74, 3902 (1952).

A mixture of 6.6 g. of 3,3-dibromo-1,1,1-trifluoropropanone, 60 ml. of water, and 6.6 g. sodium acetate was refluxed for about 10 minutes. The solution thus obtained was cooled and added dropwise to a solution of 6 g. of aminoacetamidine dihydrobromide in 90 ml. of methanol cooled to a temperature of about −30° C., followed by the addition of a solution of 3.6 g. of sodium hydroxide pellets in 25 ml. of water. The reaction mixture was stirred and warmed gradually to about 20° C. over a period of about two hours. The reaction product mixture was concentrated in vacuo to remove the methanol, and the residue extracted with ethyl acetate. There was obtained product weighing 3.6 g. and having a melting point of about 133°–136° C. after recrystallization from a mixture of benzene and hexane. The product was identified by NMR spectrum and elemental analyses as 2-amino-6-trifluoromethylpyrazine.

Analyses calcd. for $C_5H_4F_3N_3$:

|   | Theoretical | Found |
| --- | --- | --- |
| C | 36.82% | 37.11% |
| H | 2.47 | 2.17 |
| N | 25.76 | 25.52 |

Preparation 30

2-Amino-5-trifluoromethylpyrazine

A solution of 18 g. of 4,5-diamino-6-hydroxypyrimidine sulfate (commercially available) in 180 ml. of aqueous 3 N sodium hydroxide was prepared and cooled, and to the cooled mixture there was added 25.2 g. of 3,3-dibromo-1,1,1-trifluoropropanone. The reaction mixture was stirred for about 48 hours at room temperature. The precipitate which formed was filtered off, dissolved in 140 ml. of aqueous 60% sulfuric acid, and heated at about 135° C. for about 8 hours. The reaction mixture was poured over crushed ice and the aqueous mixture neutralized using concentrated aqueous ammonium hydroxide. The solution was then extracted with ethyl acetate. The ethyl acetate extracts were concentrated in vacuo to dryness and the residue recrystallized from a mixture of benzene and hexane to yield product weighing 2.2 g., and having a melting point of about 118°–122° C. The product was identified by NMR spectrum and elemental analyses as 2-amino-5-trifluoromethylpyrazine.

Analyses calcd. for $C_5H_4F_3N_3$:

|   | Theoretical | Found |
| --- | --- | --- |
| C | 36.82% | 37.04% |
| H | 2.47 | 2.58 |
| N | 25.76 | 25.97 |

Preparation 31

2-Amino-5-phenyl-6-trifluoromethylpyrazine

This intermediate was prepared stepwise.

Following the procedure of Lombardino, *J. Het. Chem.*, 10, 697 (1973), there was prepared 1-phenyl-3,3,3-trifluoro-1,2-propanedione monohydrate.

To a solution of 1.8 g. of 1-phenyl-3,3,3-trifluoro-1,2-propanedione monohydrate in 40 ml. of methanol, cooled in an ice bath, there was added, with stirring, 2 g. of aminoacetamidine dihydrobromide. Stirring was continued while 8.6 ml. of aqueous 2 N sodium hydroxide was added. The reaction mixture was then stirred at room temperature for about two hours, and then stirred and refluxed for about four hours. The reaction mixture was cooled and acidified with dilute aqueous hydrochloric acid. Water was added, and the mixture extracted with 100 ml. of ethyl acetate. The ethyl acetate extract was dried over anhydrous magnesium sulfate, the drying agent filtered off, and the filtrate concentrated in vacuo. The residue thus obtained was dissolved in chloroform, and chromatographed on a silica gel column using chloroform as the eluant. There was obtained material weighing 100 mg., and identified as 2-amino-5-phenyl-6-trifluoromethylpyrazine.

Preparation 32

2-Amino-5-(4-bromophenyl)-6-chloropyrazine

This compound was prepared stepwise.

Step 1. A mixture of 37 g. of 1-(4-bromophenyl)-1,2-propanedione-2-oxime, 34 g. of the tosylate salt of ethyl aminocyanoacetate, and 750 ml. isopropanol was stirred at room temperature for about 6 days. Another 12 g. of the above-identified tosylate salt was added to the reaction mixture and stirring at room temperature continued for 24 hours. Another 3 g. of the tosylate salt was added to the reaction mixture and stirring continued at room temperature for several more days. The reaction mixture was cooled, and the solid which precipitated was filtered off. The solid was extracted with 2 liters of boiling ethyl acetate, and the solid filtered off. The filtrate was concentrated in vacuo to about 900 ml. The solution was filtered again and then cooled. The crystalline material which separated was filtered off. It had a melting point of about 200°–205° C., and was identified by NMR spectrum as 2-amino-5-(4-bromophenyl)-3-carbethoxypyrazine-1-oxide. Yield: 11 g.

Step 2. A mixture of 60 ml. of phosphorus oxychloride, 10 ml. dimethylformamide was stirred and 12.1 g. of 2-amino-5-(4-bromophenyl)-3-carbethoxypyrazine-1-oxide (prepared as above) added in small amounts. When the addition was complete, the reaction mixture was stirred at reflux for about 15 minutes, after which the excess phosphorus oxychloride was removed in vacuo. Ice was added very carefully to the residue, and the mixture made basic by adding solid sodium bicarbonate. The mixture was extracted with 800 ml. of chloroform and the chloroform extract dried over anhydrous magnesium sulfate. The drying agent was filtered off and the filtrate concentrated to dryness in vacuo to leave a black solid. The black solid was extracted with 4×500 ml. portions of boiling cyclohexane. The combined cyclohexane extracts were combined and concentrated to a volume of about 300 ml. A beige solid separated which had a melting point of about 151°–153° C., and which was identified by NMR spectrum as 5-(4-bromophenyl)-3-carbethoxy-6-chloro-2-{[(dimethylamino)methylene]imino}pyrazine. Yield: 10.5 g.

Step 3. A mixture of 12 g. of 5-(4-bromophenyl)-3-carbethoxy-6-chloro-2-{[(dimethylamino)methylene]imino}pyrazine (prepared as in Step 2, above) and 150 ml. of aqueous 2 N hydrochloric acid was stirred and refluxed for about 5 minutes, during which time a white precipitate formed. The mixture was cooled and about 50 ml. of aqueous 1 N sodium hydroxide solution was added. The mixture was filtered and the solid which was collected on the filter was washed with water. A sample of the solid recrystallized from ethanol had a melting point of about 207°–208° C., and was identified by NMR spectrum and elemental analyses as 2-amino-5-(4-bromophenyl)-3-carbethoxy-6-chloropyrazine. Yield: 10 g.

Analyses calculated for $C_{13}H_{11}BrClN_3O_2$:

|   | Theoretical | Found |
|---|---|---|
| C | 43.79 | 43.90 |
| H | 3.11 | 3.33 |
| N | 11.78 | 11.59 |

Step 4. A mixture of 10 g. of the 2-amino-5-(4-bromophenyl)-3-carbethoxy-6-chloropyrazine, 75 ml. of dioxane, 75 ml. of water, and 8 g. of sodium hydroxide pellets was heated briefly to refluxing, at which time complete solution was obtained. The mixture was acidified with acetic acid and cooled. The solid which separated was filtered off and slurried with aqueous 1 N hydrochloric acid. The mixture was filtered to collect the solid product. A sample recrystallized from ethanol had melting point of about 212°–214° C., and was identified by NMR spectrum and elemental analyses at 2-amino-5-(4-bromophenyl)-3-carboxy-6-chloropyrazine. Yield: 9 g.

Analyses calculated for $C_{11}H_7BrClN_3O_2$:

|   | Theoretical | Found |
|---|---|---|
| C | 40.21 | 40.10 |
| H | 2.15 | 2.23 |
| N | 12.79 | 12.63 |

Step 5. A mixture of 9 g. of 2-amino-5-(4-bromophenyl)-3-carboxy-6-chloropyrazine and 50 ml. of tetralin was refluxed for about 15 minutes. The mixture was cooled and 75 ml. of hexane was added. The solid which separated was filtered off and washed with hexane. The solid was recrystallized from ethyl acetate to yield product having a melting point of about 254°–256° C. and identified by NMR spectrum as 2-amino-5-(4-bromophenyl)-6-chloropyrazine. Yield: 4 g.

The syntheses of the novel compounds of formula I are exemplified by the following examples, but the scope of the invention is not to be considered as limited thereby.

EXAMPLE 1

1-(2-Chlorobenzoyl)-3-[5-(4-bromophenyl)-6-methyl-2-pyrazinyl]urea

To a mixture of 2.6 g. of 2-amino-5-(4-bromophenyl)-6-methylpyrazine in 100 ml. of ethyl acetate was added 2.0 g. of 2-chlorobenzoylisocyanate and the mixture stirred overnight at room temperature. The mixture was filtered. The solid material which was collected upon the filter was recrystallized from ethanol to yield product having a melting point of about 230°–232° C. The product was identified by elemental analyses and NMR and infrared spectra as 1-(2-chlorobenzoyl)-3-[5-(4-bromophenyl)-6-methyl-2-pyrazinyl]urea.

Analyses calcd. for $C_{19}H_{18}BrClN_4O_2$:

|   | Theoretical | Found |
|---|---|---|
| C | 51.20% | 51.03% |
| H | 3.17 | 3.37 |
| N | 12.57 | 12.62 |

Following the general procedure of Example 1, and using appropriate starting materials, the following additional compounds were prepared and identified by elemental analyses, NMR, and infrared spectra.

1A. 1-(2-Chlorobenzyl)-3-(5-trifluoromethyl-2-pyrazinyl)urea, having a melting point of about 219°–220° C., from 500 mg. of 2-amino-5-trifluoromethylpyrazine and 600 mg. of 2-chlorobenzoylisocyanate.

1B. 1-(2-Chlorobenzoyl)-3-(5-phenyl-2-pyrazinyl)urea, having a melting point of about 222°–224° C., from 1.0 g. of 2-amino-5-phenylpyrazine and 1.0 g. of 2-chlorobenzoylisocyanate.

1C. 1-(2-Bromobenzoyl)-3-[5-(4-bromophenyl)-6-methyl-2-pyrazinyl]urea, having a melting point of about 220°–222° C., from 2.0 g. of 2-amino-5-(4-bromophenyl)-6-methylpyrazine and 2.0 g. of 2-bromobenzoylisocyanate.

1D. 1-[5-(4-Bromophenyl)-6-methyl-2-pyrazinyl]-3-(2-methylbenzoyl)urea, having a melting point of about 247°–248° C., from 1.0 g. of 2-amino-5-(4-bromophenyl)-6-methylpyrazine and 1.0 g. of 2-methylbenzoylisocyanate.

1E. 1-(2-Chlorobenzoyl)-3-[5-(4-ethylphenyl)-6-methyl-2-pyrazinyl]urea, having a melting point of about 212°–214° C., from 500 mg. of 2-amino-5-(4-ethylphenyl)-6-methylpyrazine and excess 2-chlorobenzoylisocyanate.

1F. 1-(2-Chlorobenzoyl)-3-(6-chloro-2-pyrazinyl)urea, having a melting point of about 202°-203° C., from 1.5 g. of 2-amino-6-chloropyrazine and 2.0 g. of 2-chlorobenzoylisocyanate.

1G. 1-(2-Chlorobenzoyl)-3-(6-trifluoromethyl-2-pyrazinyl)urea, having a melting point of about 179°-180° C., from 1.5 g. of 2-amino-6-trifluoromethylpyrazine and 1.6 g. of 2-chlorobenzoylisocyanate.

1H. 1-(2-Chlorobenzoyl)-3-[5-(4-methylphenyl)-2-pyrazinyl]urea, having a melting point of about 230°-232° C., from 600 mg. of 2-amino-5-(4-methylphenyl)pyrazine and 600 mg. of 2-chlorobenzoylisocyanate.

1I. 1-(2-Chlorobenzoyl)-3-[5-(4-chlorophenyl)-6-methyl-2-pyrazinyl]urea, having a melting point of about 228°-229° C., from 600 mg. of 2-amino-5-(4-chlorophenyl)-6-methylpyrazine and 1.0 g. of 2-chlorobenzoylisocyanate.

1J. 1-(2-Chlorobenzoyl)-3-(6-methyl-5-phenyl-2-pyrazinyl)urea, having a melting point of about 221°-222° C., from 500 mg. of 2-amino-6-methyl-5-phenylpyrazine and excess 2-chlorobenzoylisocyanate.

1K. 1-(2-Bromobenzoyl)-3-(5-trifluoromethyl-2-pyrazinyl)urea, having a melting point of about 206°-208° C., from 300 mg. of 2-amino-5-trifluoromethylpyrazine and 500 mg. of 2-bromobenzoylisocyanate.

1L. 1-(2-Chlorobenzoyl)-3-[5-(4-bromophenyl)-6-chloro-2-pyrazinyl]urea, weighing 1.4 g., and having a melting point of about 240°-242° C., from 0.9 g. of 2-amino-5-(4-bromophenyl)-6-chloropyrazine and 0.65 g. of 2-chlorobenzoylisocyanate.

EXAMPLE 2

1-(2-Chlorobenzoyl)-3-[5-(4-chlorophenyl)-2-pyrazinyl]urea

To a solution of 0.5 g. of 2-amino-5-(4-chlorophenyl)pyrazine in 30 ml. of dimethylformamide there was added 0.95 g. of 2-chlorobenzoylisocyanate, and the mixture was stirred at ambient room temperature for about 3-4 hours. At the end of that time the solution was poured on crushed ice and the precipitate which formed was collected and washed with water. The crude material, which weighed 950 mg., was recrystallized twice from a mixture of ethyl acetate and a small amount of dimethylformamide to yield product weighing 200 mg., and having a melting point of about 231°-234° C. This product was identified by elemental analyses and NMR spectrum as 1-(2-Chlorobenzoyl)-3-[5-(4-chlorophenyl)-2-pyrazinyl]urea.

Analyses calculated for $C_{18}H_{16}Cl_2N_4O_2$:

|   | Theoretical | Found |
|---|---|---|
| C | 55.82 | 56.08 |
| H | 3.12 | 3.07 |
| N | 14.47 | 14.58 |

Following the general procedure of Example 2, and using appropriate starting materials, the following additional compounds were prepared and identified by elemental analyses and NMR spectra.

2A. 1-(2-Chlorobenzoyl)-3-[6-methyl-5-(α,α,α-trifluoro-m-tolyl)-2-pyrazinyl]urea, having a melting point of about 202°-204° C., and weighing 0.95 g., was obtained from 1.0 g. of 2-amino-5-(α,α,α-trifluoro-m-tolyl)-6-methylpyrazine and 1.3 g. of 2-chlorobenzoylisocyanate.

2B. 1-(2-Chlorobenzoyl)-3-[5-(4-methoxyphenyl)-6-methyl-2-pyrazinyl]urea, having a melting point of about 218°-221° C., and weighing 0.5 g., from 0.6 g. of 2-amino-5-(4-methoxyphenyl)-6-methylpyrazine and 0.95 g. of 2-chlorobenzoylisocyanate.

2C. 1-(2-Chlorobenzoyl)-3-[5-(2,4-xylyl)-2-pyrazinyl]urea, having a melting point of about 218°-220° C., and weighing 1.06 g., from 0.77 g. of 2-amino-5-(2,4-xylyl)-pyrazine and 1.2 g. of 2-chlorobenzoylisocyanate.

2D. 1-(2-Methylbenzoyl)-3-[6-methyl-5-(α,α,α-trifluoro-m-tolyl)-2-pyrazinyl]urea, having a melting point of about 211°-212° C., and weighing 230 mg., was obtained from 0.5 g. of 2-amino-5-(α,α,α-trifluoro-m-tolyl)-6-methylpyrazine and 0.75 g. of 2-methylbenzoylisocyanate.

2E. 1-[5-(4-Methoxyphenyl)-6-methyl-2-pyrazinyl]-3-(2-methylbenzoyl)urea, having a melting point of about 235°-238° C., and weighing 400 mg., from 0.6 g. of 2-amino-5-(4-methoxyphenyl)-6-methylpyrazine and 1.0 g. of 2-methylbenzoylisocyanate.

2F. 1-(2-Chlorobenzoyl)-3-[6-methyl-5-(4-methylphenyl)-2-pyrazinyl]urea, having a melting point of about 216°-217° C., and weighing 0.7 g., from 0.6 g. of 2-amino-6-methyl-5-(4-methylphenyl)pyrazine and 0.8 g. of 2-chlorobenzoylisocyanate.

2G. 1-[5-(4-Bromophenyl)-2-pyrazinyl]-3-(2-chlorobenzoyl)urea, having a melting point of about 227°-231° C., and weighing 0.7 g., from 0.7 g. of 2-amino-5-(4-bromophenyl)pyrazine and 1.0 g. of 2-chlorobenzoylisocyanate.

2H. 1-[5-(4-Bromophenyl)-6-ethyl-2-pyrazinyl]-3-(2-chlorobenzoyl)urea, having a melting point of about 208°-210° C., and weighing 270 mg., from 0.6 g. of 2-amino-5-(4-bromophenyl)-6-ethylpyrazine and 1.0 g. of 2-chlorobenzoylisocyanate.

2I. 1-(2-Chlorobenzoyl)-3-[6-methyl-5-(4-phenoxyphenyl)-2-pyrazinyl]urea, having a melting point of about 204°-207° C., and weighing 370 mg., from 0.5 g. of 2-amino-6-methyl-5-(4-phenoxyphenyl)pyrazine and 0.8 g. of 2-chlorobenzoylisocyanate.

2J. 1-(2-Chlorobenzoyl)-3-[6-methyl-5-(4-biphenylyl)-2-pyrazinyl]urea, having a melting point of about 234°-237° C., and weighing 0.58 g., from 0.85 g. of 2-amino-6-methyl-5-(4-biphenylyl)pyrazine and 0.7 g. of 2-chlorobenzoylisocyanate.

2K. 1-(2-Chlorobenzoyl)-3-[5-(4-fluorophenyl)-6-methyl-2-pyrazinyl]urea, having a melting point of about 211°-212° C., and weighing 0.7 g., from 0.6 g. of 2-amino-5-(4-fluorophenyl)-6-methylpyrazine and 0.6 g. of 2-chlorobenzoyl isocyanate.

2L. 1-(2-Chlorobenzoyl)-3-[5-(4-fluorophenyl)-2-pyrazinyl]urea, weighing 0.2 g., and having a melting point of about 230°-234° C., from 0.5 g. of 2-amino-5-(4-fluorophenyl)pyrazine and 0.5 g. of 2-chlorobenzoyl isocyanate.

2M. 1-(2-Chlorobenzoyl)-3-[5-(α,α,α-trifluoro-p-tolyl)-2-pyrazinyl]urea, having a melting point of about 213°-215° C., and weighing 0.6 g., from 0.6 g. of 2-amino-5-(α,α,α-trifluoro-p-tolyl)pyrazine and 0.55 g. of 2-chlorobenzoyl isocyanate.

EXAMPLE 3

1-[5-(3-Bromophenyl)-6-methyl-2-pyrazinyl]-3-(2-chlorobenzoyl)urea

A suspension of 0.7 g. of 2-amino-5-(3-bromophenyl)-6-methylpyrazine in 10 ml. of dichloroethane under dry nitrogen was prepared and there was added thereto with stirring 0.52 g. of 2-chlorobenzoyl isocyanate. A solid precipitate formed immediately. After stirring the mixture for about 30 minutes, the solid was filtered off and recrystallized from a mixture of commercial absolute ethanol and dimethylformamide. There was obtained product having a melting point of about 201°–203° C., and weighing 370 mg. It was identified by NMR spectrum and elemental analyses as 1-[5-(3-bromophenyl)-6-methyl-2-pyrazinyl]-3-(2-chlorobenzoyl)urea.

Analyses calculated for $C_{19}H_{15}BrClN_4O_2$:

|   | Theoretical | Found |
|---|---|---|
| C | 51.20 | 51.24 |
| H | 3.17 | 3.44 |
| N | 12.57 | 12.77 |

Following the same general procedure as in Example 3, and using appropriate starting materials, the following additional compounds were prepared and identified by elemental analyses and NMR spectrum.

3A. 1-(2-Chlorobenzoyl)-3-(5-cyclohexyl-6-methyl-2-pyrazinyl)urea, having a melting point of about 203°–205° C., and weighing 1.0 g., from 0.6 g. of 2-amino-5-cyclohexyl-6-methylpyrazine and 0.63 g. of 2-chlorobenzoyl isocyanate.

3B. 1-(2-Chlorobenzoyl)-3-[5-(4-methylthiophenyl)-6-methyl-2-pyrazinyl]urea, having a melting point of about 215°–216° C., and weighing 0.7 g., from 0.7 g. of 2-amino-5-(4-methylthiophenyl)-6-methylpyrazine and 0.6 g. of 2-chlorobenzoyl isocyanate.

3C. 1-(2-Chlorobenzoyl)-3-[6-methyl-5-(2-tolyl)-2-pyrazinyl]urea, weighing 0.22 g., and having a melting point of about 206°–207° C., from 0.35 g. of 2-amino-6-methyl-5-(2-tolyl)pyrazine and 0.4 g. of 2-chlorobenzoyl isocyanate.

The compounds of formula I are useful for the control of insects of various orders, including Coleoptera such as Mexican bean beetle, boll weevil, corn rootworm, cereal leaf beetle, flea beetles, borers, Colorado potato beetle, grain beetles, alfalfa weevil, carpet beetle, confused flour beetle, powder post beetle, wireworms, rice weevil, rose beetle, plum curculio, white grubs; Diptera, such as house fly, yellow fever mosquito, stable fly, horn fly, blowfly, cabbage maggot, carrot rust fly; Lepidoptera, such as Southern armyworm, codling moth, cutworm, clothes moth, Indian meal moth, leaf rollers, corn earworm, European corn borer, cabbage worm, cabbage looper, cotton bollworm, bagworm, eastern tent caterpillar, sod webworm, fall armyworm; and Orthoptera, such as German cockroach and American cockroach.

It has been found that the novel compounds of formula I interfere with the mechanism of metamorphosis which occurs in insects, causing the death of the insects.

It has also been found that compounds of formula I wherein

A is bromo or chloro;

$R^1$ is hydrogen, trifluoromethyl, or

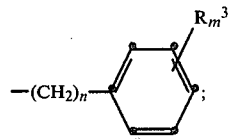

$R^2$ is hydrogen, chloro, methyl, or trifluoromethyl;

$R^3$ is hydrogen, halo, methoxy, trifluoromethyl, or phenyl;

m is 0 or 1; and n is 0, have ovicidal activity.

The novel compounds of formula I are therefore useful in a method for the control of insects of an order selected from the group consisting of Coleoptera, Diptera, Lepidoptera, and Orthoptera, which comprises applying to the loci of the insects an insecticidally-effective amount of a 1-(mono-o-substituted benzoyl)-3-(substituted pyrazinyl)urea of formula I.

The insecticidal method is practiced by applying to the loci of the insects an insecticidal composition which comprises an insecticidally-effective amount of a compound of formula I and a solid or liquid carrier.

The novel compounds of formula I are formulated for use as insecticides by being mixed with a solid carrier material or dissolved or dispersed in a liquid carrier material. Included in such mixtures, if desired, are adjuvants such as surface-active substances and stabilizers.

These formulations can include aqueous solutions and dispersions, oil solutions and oil dispersions, pastes, dusts, wettable powders, miscible oils, granules, aerosol preparations and the like.

The wettable powders, pastes and miscible oils are formulations in concentrated form which are diluted with water before or during use.

The granular preparations are produced by taking up the novel compound in a solvent, after which granular carrier material such as porous granules, for example, pumice or attapulgite clay; mineral non-porous granules, such as sand or ground marl; or organic granules are impregnated with the solution, suitably in the presence of a binder. Such preparations contain from about 1 to about 15 percent active ingredient, suitably about 5 percent.

Dust formulations are prepared by intimately mixing the active compound with an inert solid carrier material in a concentration of, for example, from about 1 to about 50 percent by weight. Examples of suitable solid carrier materials include talc, kaolin, diatomaceous earth, dolomite, gypsum, chalk, bentonite, and attapulgite, or mixtures of these and similar substances. It is also possible to use organic carrier materials such as ground walnut shells.

Wettable powder formulations are produced by mixing from about 10 to about 80 parts by weight of a solid inert carrier, such as one of the aforementioned carrier materials, with from about 10 to about 80 parts by weight of the active compound, together with from about 1 to about 5 parts by weight of a dispersing agent, such as for example, the ligninsulfonates or alkylnaphthalenesulfonates, and preferably also with from about 0.5 to about 5 parts by weight of a wetting agent, such as one of the fatty alcohol sulfates, alkylarylsulfonates, or fatty acid condensation products.

Miscible oil formulations are prepared by dissolving the active compound in or suspending the active compound in a suitable solvent which is preferably rather immiscible with water, after which an emulsifier is added to the preparation. Suitable solvents include xylene, toluene, and high aromatic petroleum distillates, for example solvent naphtha, distilled tar oil, and mixtures of these. Suitable emulsifiers include alkylphenoxypolyglycol ethers, polyoxyethylene sorbitan esters of fatty acids, or polyoxyethylene sorbitol esters of fatty acids. These miscible oils contain the active compound in a concentration of from about 2 percent to about 50 percent by weight.

When an aerosol preparation is desired, such aerosol preparation can be obtained in the usual manner by incorporating the active compound in a solvent in a volatile liquid suitable for use as a propellant, for example, one of the commercially available fluorocarbon propellants.

As is well understood, the preparations containing one of the active compounds of formula I may also include other known pesticidal compounds. This of course broadens the spectrum of activity of the preparation.

The amount of 1-(mono-o-substituted benzoyl)-3-(substituted pyrazinyl)urea to be applied for insect control purposes to a given area of plant life is, of course, dependent upon a variety of factors, such as the extent of vegetative surface to be covered, the severity of the insect infestation, the condition of the foliage treated, the temperature, the humidity, etc. In general, however, the application of the active ingredient in a formulation containing a concentration of the active ingredient of from about 0.1 to about 1000 ppm. is desirable.

The insecticidal activity of the novel compounds of formula I has been determined by testing the efficacy of formulations of the compounds against Mexican bean beetle larvae (*Epilachna varivestia*), and against Southern armyworm larvae (*Spodoptera eridania*) in an insecticide screen. These insects are members of the Coleoptera and Lepidoptera orders of insects, respectively. The compounds have been tested in several tests against these insects at rates of from about 1000 ppm. down to about 1 ppm., the compounds being applied at these rates to leaves of plants upon which the above-identified larvae feed.

Experiment 1

The following procedure was used to evaluate the efficacy of the novel compounds of formula I as insecticides.

Bean plants were grown in four-inch square pots, with there being 6 to 10 plants per pot. When the plants were 10 days old, they were ready for use in this experiment.

Each test compound was formulated by dissolving 10 mg. of the test compound in 1 ml. of solvent (23 g. Toximul R plus 13 g. Toximul S per liter of 1:1 anhydrous ethanol and acetone) followed by mixing with 9 ml. of water to give a 1000 parts per million (ppm.) concentration of the test compound in the solution. (Toximul R and Toximul S are each a sulfonate/nonionic blend produced by Stepan Chemical Company, Northfield, Illinois.) A portion of the 1000 ppm. concentration of test solution of each compound was then diluted in the ratio of 1:10 with the stated solvent to provide a test solution having a concentration of 100 ppm. The solution of test compound, at each concentration, was then sprayed onto the bean plants in each pot. The plants were allowed to dry and then 12 leaves were removed and the cut ends wrapped in water-soaked cellucotton. The leaves were divided between six 100×20 mm. plastic Petri dishes. Five second-instar Mexican bean beetle larvae (*Epilachna varivestis*) and five second- and third-instar Southern armyworm larvae (*Spodoptera eridania*) were placed in each of three dishes. The dishes were then placed in a room wherein the temperature and relative humidity were controlled at about 78° F. and about 51 percent, respectively, for a period of about four days, at which time the first evaluation of the effects of the test compounds were made. After this evaluation, two fresh leaves from the original treated pots were placed in each dish. The dishes were again maintained in the temperature and humidity controlled room for an additional three days until the final seven day evaluation was made.

The percent control was determined by counting the number of living larvae per dish. All the treatments were compared to solvent controls and nontreated controls. The rating code (percent of control) used was as follows:

0=0%
1=1-50%
2=51-99%
3=100% control

The results of this test are set forth in Table 1, which follows. In the table, column 1 identifies the compounds by the number of the preparative example; column 2, the application rate in parts per million (ppm.); and columns 3 through 6 give the Rating Code at days 4 and 7 for the two insects against which the compounds were tested at the application rates of 1000 ppm. and 100 ppm.

TABLE 1

| Compound | Appln Rate ppm. | Rating Code | | | |
|---|---|---|---|---|---|
| | | Mexican Bean Beetle | | Southern Armyworm | |
| | | Day 4 | Day 7 | Day 4 | Day 7 |
| | 1000 | 1 | 3 | 3 | 3 |
| | 100 | 1 | 2 | 3 | 3 |
| 1A | 1000 | 1 | 2 | 2 | 2 |
| | 100 | 1 | 1 | 1 | 1 |
| 1B | 1000 | 0 | 0 | 1 | 2 |
| | 100 | 0 | 0 | 0 | 1 |
| 1C | 1000 | 0 | 3 | 3 | 3 |
| | 100 | 0 | 2 | 3 | 3 |
| 1D | 1000 | 0 | 1 | 3 | 3 |
| | 100 | 0 | 0 | 3 | 3 |
| 1E | 1000 | 0 | 2 | 3 | 3 |
| | 100 | 0 | 3 | 3 | 3 |
| 1F | 1000 | 1 | 2 | 2 | 2 |
| | 100 | 0 | 1 | 0 | 0 |
| 1G | 1000 | 0 | 3 | 2 | 2 |
| | 100 | 0 | 2 | 0 | 0 |
| 1H | 1000 | 0 | 0 | 1 | 0 |
| | 100 | 0 | 0 | 0 | 0 |
| 1I | 1000 | 0 | 2 | 3 | 3 |
| | 100 | 0 | 1 | 3 | 3 |
| 1J | 1000 | 0 | 1 | 3 | 3 |
| | 100 | 0 | 0 | 2 | 2 |
| 1K | 1000 | 2 | 2 | 2 | 2 |
| | 100 | 2 | 2 | 2 | 2 |
| 1L | 1000 | 0 | 2 | 3 | 3 |
| | 100 | 0 | 0 | 3 | 3 |
| 2 | 1000 | 0 | 0 | 3 | 3 |
| | 100 | 0 | 0 | 3 | 3 |
| 2B | 1000 | 2 | 3 | 2 | 3 |
| | 100 | 1 | 2 | 2 | 3 |
| 2C | 1000 | 0 | 0 | 1 | 1 |
| | 100 | 0 | 0 | 0 | 0 |
| 2D | 1000 | 1 | 2 | 3 | 3 |
| | 100 | 0 | 1 | 3 | 3 |
| 2E | 1000 | 0 | 1 | 3 | 3 |
| | 100 | 0 | 0 | 2 | 3 |

TABLE 1-continued

| Compound | Appln Rate ppm. | Rating Code Mexican Bean Beetle Day 4 | Day 7 | Southern Armyworm Day 4 | Day 7 |
|---|---|---|---|---|---|
| 2F | 1000 | 2 | 3 | 2 | 3 |
|  | 100 | 2 | 3 | 2 | 2 |
| 2G | 1000 | 0 | 0 | 3 | 3 |
|  | 100 | 0 | 0 | 2 | 3 |
| 2H | 100 | 0 | 0 | 2 | 3 |
|  | 100 | 0 | 0 | 0 | 1 |
| 2I | 1000 | 2 | 2 | 2 | 2 |
|  | 100 | 1 | 2 | 1 | 1 |
| 2J | 1000 | 0 | 1 | 3 | 3 |
|  | 100 | 0 | 0 | 0 | 1 |
| 3 | 1000 | 0 | 3 | 3 | 3 |
|  | 100 | 0 | 1 | 2 | 2 |
| 3A | 1000 | 1 | 3 | 3 | 3 |
|  | 100 | 0 | 2 | 3 | 3 |
| 3B | 1000 | 1 | 3 | 2 | 3 |
|  | 100 | 0 | 1 | 0 | 2 |

Experiment 2

Several of the novel compounds tested in Experiment 1, above, were retested, this time at lower levels of application. The preparation of the bean plants was the same. The test compounds were formulated in the manner described hereinbelow:

Ten mg. of test compound was dissolved in 1 ml. of solvent and mixed with 9 ml. of water to give a 1000 ppm. solution.

This solution was then serially diluted to obtain the necessary concentrations of solution for conducting the tests.

The solvent used was 50:50 alcohol:acetone plus 23 g. of Toximul R and 13 g. of Toximul S per liter.

The percent control was determined by counting the number of living larvae of Southern armyworm (*Spodoptera eridania*) per dish and using Abbott's formula [W. W. Abbott, "A Method of Computing the Effectiveness of an Insecticide", *J. Econ. Entomol.* 18, 265–7 (1925)]:

$$\text{Percent Control} = \frac{\text{No. of survivors in control} - \text{No. of survivors in treatment} \times 100}{\text{No. survivors in control}}$$

The results are set forth in Table 2, which follows. Where more than one replicate was run the recorded results are averages.

TABLE 2

| Compound | Appln. Rate ppm | Percent Control Southern Armyworm Day 4 | Day 7 |
|---|---|---|---|
| 1 | 100 | 100 | 100 |
|  | 50 | 100 | 100 |
|  | 25 | 100 | 100 |
|  | 10 | 95 | 100 |
|  | 5 | 57 | 96 |
|  | 2.5 | 54 | 93 |
|  | 1.0 | 17 | 76 |
|  | 0.5 | 0 | 20 |
| 1C | 100 | 100 | 100 |
|  | 50 | 100 | 100 |
|  | 25 | 100 | 100 |
|  | 10 | 100 | 100 |
|  | 5 | 100 | 100 |
|  | 2.5 | 100 | 100 |
|  | 1.0 | 60 | 93 |
|  | 0.5 | 20 | 73 |
| 1D | 100 | 100 | 100 |
|  | 50 | 100 | 100 |
|  | 25 | 100 | 100 |
|  | 10 | 100 | 100 |
|  | 5 | 100 | 100 |
|  | 2.5 | 100 | 100 |
|  | 1.0 | 33 | 67 |
|  | 0.5 | 7 | 27 |
| 1E | 100 | 100 | 100 |
|  | 50 | 100 | 100 |
|  | 25 | 100 | 100 |
|  | 10 | 81 | 93 |
|  | 5 | 80 | 100 |
|  | 2.5 | 27 | 47 |
| 1I | 100 | 100 | 100 |
|  | 50 | 100 | 100 |
|  | 25 | 100 | 100 |
|  | 10 | 100 | 100 |
|  | 5 | 96 | 100 |
|  | 2.5 | 80 | 100 |
|  | 1.0 | 20 | 73 |
|  | 0.5 | 0 | 53 |
| 1L | 10 | 100 | 100 |
|  | 5 | 13 | 75 |
| 2 | 100 | 100 | 100 |
|  | 50 | 93 | 100 |
|  | 25 | 93 | 100 |
|  | 10 | 57 | 100 |
|  | 5 | 30 | 76 |
|  | 2.5 | 13 | 27 |
|  | 1.0 | 0 | 0 |
|  | 0.5 | 7 | 7 |
| 2A | 100 | 100 | 100 |
|  | 50 | 100 | 100 |
|  | 25 | 100 | 100 |
|  | 10 | 100 | 100 |
|  | 5 | 100 | 100 |
|  | 2.5 | 93 | 100 |
|  | 1.0 | 20 | 80 |
|  | 0.5 | 23 | 40 |
| 2B | 100 | 93 | 100 |
|  | 50 | 100 | 100 |
|  | 25 | 86 | 93 |
|  | 10 | 27 | 73 |
| 2D | 100 | 100 | 100 |
|  | 50 | 100 | 100 |
|  | 25 | 100 | 100 |
|  | 10 | 100 | 100 |
|  | 5 | 100 | 100 |
|  | 2.5 | 100 | 100 |
|  | 1.0 | 53 | 100 |
| 2E | 100 | 100 | 100 |
|  | 50 | 100 | 100 |
|  | 25 | 100 | 100 |
|  | 10 | 86 | 100 |
|  | 5 | 27 | 73 |
|  | 2.5 | 27 | 47 |
|  | 1.0 | 20 | 27 |
| 2F | 100 | 100 | 100 |
|  | 50 | 87 | 93 |
|  | 25 | 93 | 100 |
|  | 10 | 67 | 93 |
| 2G | 100 | 100 | 100 |
|  | 50 | 93 | 100 |
|  | 25 | 100 | 100 |
|  | 10 | 80 | 100 |
| 2K | 10 | 100 | 100 |
|  | 5 | 20 | 73 |
| 3A | 10 | 67 | 100 |
|  | 5 | 0 | 27 |

Experiment 3

One of the compounds coming within the scope of generic formula I, supra, was also tested against Egyptian cotton leaf worm larvae (*Spodoptera littoralis*).

The test compound, technical material, was dissolved in acetone and the solution diluted with water containing a surfactant.

Cauliflower plants were sprayed with the thus formulated compound in the field. Leaves were collected and fed in the laboratory to field-collected Egyptian cotton leaf worm larvae, 1st–3rd instars. Mortality at 4 days and 7 days feeding at rates from 100 ppm. downward was recorded, and appears in Table 3, which follows. The test compound is identified by the number of its preparative example.

TABLE 3

| Compound | Appln. Rate ppm. | Percent Mortality 2nd Instar Larvae of Egyptian cotton leaf worm | |
|---|---|---|---|
| | | Day 4 | Day 7 |
| 1 | 100 | 90 | 100 |
| | 75 | 80 | 100 |
| | 50 | 90 | 100 |
| | 25 | 70 | 100 |

After the 7 day reading, additional cauliflower leaves were collected in the field from selected treatments, and the residual activity determined by 4 and 7 day observations made in the same way as described above. The results are recorded in Table 4, which follows.

TABLE 4

| Compound | Appln. Rate ppm. | Percent Mortality 2nd Instar Larvae of Egyptian cotton leaf worm | |
|---|---|---|---|
| | | Day 4 | Day 7 |
| 1 | 100 | 40 | 100 |
| | 75 | 80 | 100 |
| | 50 | 40 | 100 |
| | 25 | 0 | 80 |

Experiment 4

This experiment was conducted to determine the local systemic activity of several compounds of the instant application.

The test compounds were each formulated as a 50 WP (50% wettable powder). Each formulation was diluted with water to give the desired concentration of test material.

Soybean seeds (variety Calland) were planted and allowed to germinate. Seven days after planting, when the cotyledonary leaves had formed, the soybean plants were sprayed to runoff with the test materials, and the plants were returned to the greenhouse for one week. At the end of the week, the plants were harvested and sectioned, and the cotyledonary leaves (sprayed leaves) were separated from the new growth, or the trifoliate leaves (new leaves), which developed in the 7-day period after spraying.

The sprayed leaves were placed in a Petri dish with second and third instar larvae of Southern armyworm (*Spodoptera eridania*); and the new leaves were placed in separate Petri dishes with second and third instar larvae of Southern armyworm. The dishes were placed in a room wherein the temperature and humidity were controlled at about 78° F. and about 51 percent, respectively.

After four days, the larvae were observed to determine the effects of the test compounds. After this evaluation, the surviving larvae from the treated and the new leaves, respectively, were transferred to clean Petri dishes containing untreated soybean leaves. The dishes were again maintained in the temperature and humidity controlled room for an additional three days until the final seven day evaluation was made.

The percent control was determined in the same manner as described in Experiment 2, above, using the same formula. The results are recorded in Table 5, which follows.

In the table, Column 1 identifies the test compound by the number of its preparative example in the Specification; Column 2, identifies the rate of application in parts per million (ppm.); Columns 3 and 4, the percent control on sprayed and new foliage, respectively, on Day 4; and Column 5 and 6, the percent control on sprayed and new foliage, respectively, on Day 7.

TABLE 5

| Compound | Appln. Rate ppm. | Percent Control Southern Armyworm | | | |
|---|---|---|---|---|---|
| | | Day 4 | | Day 7 | |
| | | Sprayed | New | Sprayed | New |
| 1 | 1000 | 100 | 78 | 100 | 100 |
| | 100 | 100 | 22 | 100 | 94 |
| | 10 | 29 | 0 | 88 | 28 |
| 1C | 1000 | 100 | 94 | 100 | 94 |
| | 100 | 100 | 55 | 100 | 89 |
| | 10 | 47 | 0 | 100 | 22 |
| 1D | 1000 | 100 | 78 | 100 | 100 |
| | 100 | 100 | 17 | 83 | |
| | 10 | 23 | 0 | 88 | 22 |

These results show that translocation of the insecticidal test compounds occurs in soybeans.

Experiment 5

Several of the novel compounds of this invention were tested for their efficacy as insecticides against the yellow fever mosquito, *Aedes aegypti*, of the order of Diptera.

Each test compound was formulated by dissolving 10 mg. of the compound in 1 ml. of acetone and mixing with 99 ml. of water to give a concentration of 100 ppm of the compound in the test solution. The lower concentrations of test solutions needed were then obtained by serial dilution of the 100 ppm solution with water. These test solutions were then placed in 100 ml. glass beakers, or, alternatively, 6 oz. plastic containers, 40 ml. of test solution per beaker or container, and 2 beakers or containers per rate. Twenty to thirty, 24-hour mosquito larvae were placed in each beaker. The larvae were fed 10–20 mg. of pulverized Purina laboratory chow daily for 7 days. During this time the beakers or containers were maintained in a room in which the temperature and humidity were continuously controlled and recorded, as described in Experiment 1.

The percent mortalities of the mosquito larvae were determined after 7 days by visual observation of the number of living larvae. All the treatments were compared to solvent and nontreated controls. The results are set forth in Table 5, which follows.

In the table, column 1 identifies the compounds by the number of the preparative example; column 2, the application rate in ppm; and column 3, the percent mortality at the indicated test rates.

TABLE 6

Yellow Fever Mosquito Larvacide Test

| Compound | Appln. Rate ppm. | Percent Mortality |
|---|---|---|
| 1 | 0.01 | 100 |
| 1C | 0.01 | 100 |
| 1I | 0.01 | 100 |
| Solvent | — | 0 |
| Untreated | — | 0 |

Experiment 6

This experiment was conducted to determine the ovicidal activity of several compounds of the instant application using egg clusters of Southern armyworm (*Spodoptera eridania*) and Mexican bean beetle (*Epilachna varvestis*).

The egg clusters, which were on Bountiful variety bean leaves, were placed on a paper towel and sprayed at low air pressure (approximately 3 psi) using a DeVilbiss atomizer sprayer to apply the test formulations of the compounds. These formulations were prepared in the same manner as described in Experiment 1, supra. After the spraying, the eggs were blotted with towel paper and placed in plastic Petri dishes (60×15 ml.) along with a piece of moist dental wick. The egg clusters in the Petri dishes were then incubated until the non-treated controls hatched. At that time, observations were made to determine the number of eggs which hatched. The results were recorded as the percent control. These results appear in Table 7, which follows. In the table, Column 1 identifies the test compound; Column 2, the application rate in parts per million; and Column 3, the percent control achieved.

TABLE 7

| Compound | Appln. Rate ppm. | Eggs Percent Kill SAW | Eggs Percent Kill MBB |
|---|---|---|---|
| 1 | 1000 | 100 | |
|   | 500 | 100 | |
|   | 250 | 100 | |
|   | 100 | 100 | |
|   | 50 | 100 | |
| 1C | 1000 | 100 | |
|   | 500 | 100 | |
|   | 250 | 100 | |
|   | 100 | 100 | |
| 1F | 1000 | 100 | |
| 1G | 1000 | 100 | |
| 1I | 1000 | 100 | |
|   | 500 | 100 | |
|   | 250 | 100 | |
|   | 100 | 100 | |
| 1J | 1000 | 100 | |
| 1K | 1000 | 100 | |
|   | 500 | 100 | |
|   | 250 | 100 | |
|   | 100 | 100 | |
|   | 50 | 100 | |
| 2A | 1000 | 100 | |
|   | 500 | 100 | |
|   | 250 | 100 | |
|   | 100 | 100 | |
|   | 50 | 100 | |
| 2B | 1000 | 100 | |
|   | 500 | 100 | |
|   | 250 | 95 | |
|   | 100 | 100 | |
| 2J | 1000 | 100 | |
| 2K | 1000 | 100 | 100 |
|   | 500 | 100 | 96 |
|   | 250 | 100 | 96 |
|   | 100 | 100 | |
|   | 50 | 100 | |
|   | 25 | 100 | |
|   | 10 | 96 | |
|   | 5 | 100 | |
| 3 | 1000 | 100 | |

Experiment 7

One of the compounds coming within the scope of generic formula I, supra, was tested against oriental cockroaches (*Blatta orientalis*), order Orthoptera.

The test compound, technical grade 97% pure, was formulated as a 50 percent wettable powder, as follows:

| Ingredient | Percent by Weight |
|---|---|
| Compound 1 | 51.5 |
| Stepanol ME[1] | 5.0 |
| Polyfon O[2] | 5.0 |
| Zeolex 7[3] | 5.0 |
| Bordens Clay | 33.5 |

[1]Sodium lauryl sulfate (Stepan Chemical Co., Northfield, Illinois).
[2]Sugar free sodium based sulfonates of Kraft lignin (Westvaco Corp. Polychemicals Department, P.O. Box 5207, North Charleston, S. Carolina).
[3]Hydrated sodium silico aluminate (J.M. Huber Corp., Edison, New Jersey).

The wettable powder was then mixed with a dry pulverized laboratory chow mix (Rodent Lab Chow Mix No. 5001, Ralston Purina Co.). Three different mixtures were prepared containing different levels of the test compound, that is, the active ingredient (a.i.). The three test levels were: 1%, 0.5%, and 0.1%, active ingredient, respectively. A commercially available insecticide was also run at the 0.1% a.i. level. In addition, controls were run in which the lab chow contained no test compound or commercial insecticide.

The tests were run in one gallon glass jars, using two jars per treatment level of test compound and of commercial insecticide. Two control jars were used.

In each test jar there were placed 20 second and third instar oriental cockroaches (*Blatta orientalis*), together with 50 gm. of treated laboratory chow as food. The two control jars each contained 20 second and third instar oriental cockroaches and 50 gm. of untreated laboratory chow. A plastic bottle containing 250 ml. of tap water and equipped with a cotton dental wick was placed in each jar to provide moisture for the cockroaches. A piece of paper towel was placed in each jar on which paper towel the cockroaches could crawl and beneath which they could seek shelter from light.

The present mortality was determined by counting the number of living cockroaches (*Blatta orientalis*) per jar and using Abbots formula, as described in Experiment 2, above. The counts were made 4, 7, 11 and 14 days after the start of the experiment. The results appear in Table 8, which follows, and are the average of the readings on the two jars run at each test level. The test compound is identified by the number of its preparative example.

TABLE 8

| Compound | Feeding Level (a.i.) | Percent Mortality Day 4 | Day 7 | Day 11 | Day 14 |
|---|---|---|---|---|---|
| 1 | 1.0% | 0 | 60 | 72 | 88 |
|   | 0.5% | 0 | 20 | 35 | 63 |
|   | 0.1% | 0 | 0 | 0 | 0 |

TABLE 8-continued

| Compound | Feeding Level (a.i.) | Percent Mortality | | | |
|---|---|---|---|---|---|
| | | Day 4 | Day 7 | Day 11 | Day 14 |
| Diazinon* | 0.1% | 100 | 100 | 100 | 100 |
| Control | | 0 | 0 | 0 | 0 |

*O,O-Diethyl-O-(2-isopropyl-6-methyl-4-pyrimidyl)phosphorothionate.

The results of the tests show that the novel compounds coming within the scope of generic formula I, supra, are active against a number of insects in the larval stage, as the insects ingest the leaves, or any other part of their normal habitat, e.g., water, manure, and the like, to which the active compounds have been applied. Also, novel compounds coming within the scope of generic formula I, supra, are shown to be active as ovicidal agents.

I claim:
1. A compound of the formula

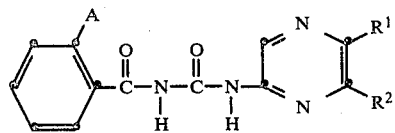

wherein
A is bromo or chloro;
$R^1$ is hydrogen, trifluoromethyl, or

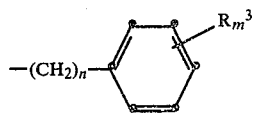

$R^2$ is hydrogen, chloro, methyl, or trifluoromethyl;
$R^3$ is hydrogen, halo, methoxy, trifluoromethyl, or phenyl;
m is 1; and
n is 0;
and 1-(2-chlorobenzoyl)-3-(5-cyclohexyl-6-methyl-2-pyrazinyl) urea.

2. The compound as in claim 1, said compound being 1-(2-chlorobenzoyl)-3-[5-(4-bromophenyl)-6-methyl-2-pyrazinyl]urea.

3. The compound as in claim 1, said compound being 1-(2-bromobenzoyl)-3-[5-(4-bromophenyl)-6-methyl-2-pyrazinyl]urea.

4. The compound as in claim 1, said compound being 1-(2-chlorobenzoyl)-3-[5-(4-chlorophenyl)-6-methyl-2-pyrazinyl]urea.

5. The compound as in claim 1, said compound being 1-(2-chlorobenzoyl)-3-[5-(4-chlorophenyl)-2-pyrazinyl]urea.

6. The compound as in claim 1, said compound being 1-(2-chlorobenzoyl)-3-[6-methyl-5-(α,α,α-trifluoro-m-tolyl)-2-pyrazinyl]urea.

7. A method for the control of ova of insects of an order selected from the group consisting of Coleoptera, Diptera, Lepidoptera, and Orthoptera, which comprises applying to the loci of the insects an insecticidally effective amount of a 1-(mono-o-substituted benzoyl)-3-(substituted pyrazinyl)urea compound of claim 1, except for 1-(2-chlorobenzoyl)-3-(5-cyclohexyl-6-methyl-2-pyrazinyl)urea.

8. The method of claim 7 wherein 1-(2-chlorobenzoyl)-3-[5-(4-bromophenyl)-6-methyl-2-pyrazinyl]urea is applied.

9. The compound as in claim 1, said compound being 1-(2-chlorobenzoyl)-3-[5-(4-methoxyphenyl)-6-methyl-2-pyrazinyl]urea.

10. The method of claim 7 wherein 1-(2-bromobenzoyl)-3-[5-(4-bromophenyl)-6-methyl-2-pyrazinyl]urea is applied.

11. The compound as in claim 1, said compound being 1-(2-chlorobenzoyl)-3-(5-cyclohexyl-6-methyl-2-pyrazinyl)urea.

12. The method of claim 7 wherein 1-(2-chlorobenzoyl)-3-[5-(4-chlorophenyl)-6-methyl-2-pyrazinyl]urea is applied.

13. The compound as in claim 1, said compound being 1-(2-chlorobenzoyl)-3-[5-(4-fluorophenyl)-6-methyl-2-pyrazinyl]urea.

14. An ovicidal composition which comprises as the active ingredient an insecticidally-effective amount of a compound of claim 1 except for 1-(2-chlorobenzoyl)-3-(5-cyclohexyl-6-methyl-2-pyrazinyl)urea formulated with a suitable carrier.

15. The ovicidal composition of claim 14 wherein the active ingredient is present in an amount from about 1 to about 15 percent by weight and the composition is formulated in granular form.

16. The ovicidal composition of claim 14 wherein the active ingredient is present in an amount from about 1 to about 50 percent by weight and the composition is formulated in dust form.

17. The ovicidal composition of claim 14 wherein the active ingredient is present in an amount from about 2 to about 50 percent by weight and the composition is formulated in miscible oil form with a suitable emulsifier.

18. The ovicidal composition of claim 14 wherein the active ingredient is present in an amount from about 10 to about 80 parts by weight and the composition is formulated in wettable powder form with an inert carrier, a dispersing agent and a wetting agent.

19. The method of claim 7 wherein 1-(2-chlorobenzoyl)-3-[5-(4-chlorophenyl)-2-pyrazinyl]urea is applied.

20. The method of claim 7 wherein 1-(2-chlorobenzoyl)-3-[6-methyl-5-(α,α,α-trifluoro-m-tolyl)-2-pyrazinyl]urea is applied.

21. The method of claim 7 wherein 1-(2-chlorobenzoyl)-3-[5-(4-methoxyphenyl)-6-methyl-2-pyrazinyl]urea is applied.

22. The method of claim 7 wherein 1-(2-chlorobenzoyl)-3-[5-(4-fluorophenyl)-6-methyl-2-pyrazinyl]urea is applied.

* * * * *